(12) United States Patent
Tong et al.

(10) Patent No.: US 9,677,097 B2
(45) Date of Patent: Jun. 13, 2017

(54) CLOSTRIDIUM CADAVERIS STRAIN AND USES OF THE SAME

(71) Applicant: GREEN CELLULOSITY CORPORATION, Hsinchu (TW)

(72) Inventors: Chiang-Hsiung Tong, Hsinchu (TW); Chang-Chieh Chen, Hsinchu (TW); Shao-Wen Wu, Hsinchu (TW); Shi-Chan Tseng, Hsinchu (TW); Hsin-Tzu Wang, Hsinchu (TW); Chin-Chen Hsu, Hsinchu (TW)

(73) Assignee: GREEN CELLULOSITY CORPORATION, Hsinchu (TW)

( * ) Notice: Subject to any disclaimer, the term of this patent is extended or adjusted under 35 U.S.C. 154(b) by 0 days.

(21) Appl. No.: 14/794,341

(22) Filed: Jul. 8, 2015

(65) Prior Publication Data
US 2016/0083755 A1 Mar. 24, 2016

Related U.S. Application Data

(60) Provisional application No. 62/021,875, filed on Jul. 8, 2014.

(51) Int. Cl.
| | | |
|---|---|---|
| *C12P 7/52* | (2006.01) |
| *C12P 7/16* | (2006.01) |
| *C12N 1/20* | (2006.01) |
| *C12N 1/36* | (2006.01) |
| *C12N 9/00* | (2006.01) |
| *C12N 15/01* | (2006.01) |
| *C12R 1/145* | (2006.01) |
| *C12N 9/04* | (2006.01) |
| *C12N 9/02* | (2006.01) |
| *C12N 9/10* | (2006.01) |
| *C12N 9/12* | (2006.01) |
| *C12N 15/52* | (2006.01) |

(52) U.S. Cl.
CPC .......... *C12P 7/52* (2013.01); *C12N 1/20* (2013.01); *C12N 1/36* (2013.01); *C12N 9/0006* (2013.01); *C12N 9/0008* (2013.01); *C12N 9/1029* (2013.01); *C12N 9/1217* (2013.01); *C12N 15/01* (2013.01); *C12N 15/52* (2013.01); *C12P 7/16* (2013.01); *C12R 1/145* (2013.01); *Y02E 50/10* (2013.01)

(58) Field of Classification Search
None
See application file for complete search history.

(56) References Cited

PUBLICATIONS

Prevost et al., "Characterization of clostridial species and sulfite-reducing anaerobes isolated from foie gras with respect to microbial quality and safety", Food Control 32 (Jul. 2013) 222-227.*

Doris Freier, Cheryle P. Mothershed, and Juergen Wiegel. Characterization of Clostridium thermocellum JW20. Applied Environmental Microbiology, Jan. 1988; vol. 54, No. 1: pp. 204-211.

* cited by examiner

*Primary Examiner* — Suzanne M Noakes
(74) *Attorney, Agent, or Firm* — Cantor Colburn LLP

(57) ABSTRACT

An isolated *Clostridium cadaveris* ITRI04005 and its uses are provided. The isolated *Clostridium cadaveris* ITRI04005 was deposited at German Collection of Microorganisms and Cell Cultures (Deutsche Sammlung von Mikroorganismen and Zellkulturen GmbH, DSMZ) under the accession number DSM 32078.

15 Claims, 7 Drawing Sheets

CLOSTRIDIUM CADAVERIS STRAIN AND USES OF THE SAME

This application claims priority to U.S. Provisional Application Ser. No. 62/021,875 filed on Jul. 8, 2014, the subject matter of which is incorporated herein by reference.

BACKGROUND

Technical Field

The present invention relates to an isolated *Clostridium cadaveris* ITRI04005 and the uses of the same, especially the uses of *Clostridium cadaveris* ITRI04005 in the production of an organic compound via fermentation and in genetic modification including (1) providing a genetically modified strain being able to express an exogenous gene or having an endogenous gene with an enhanced expression level, wherein each of the exogenous gene and the endogenous gene is a gene of an enzyme involved in an alcohol production pathway; (2) providing a genetically modified strain that has an endogenous gene with an attenuated expression level or without any expression level, wherein the endogenous gene is a gene of an enzyme participating in synthesis of acetic acid; (3) and providing a genetically modified strain being able to express an exogenous gene or having an endogenous gene with an enhanced expression level, wherein each of the exogenous gene and the endogenous gene is a gene of a heat shock protein (HSP).

Descriptions of the Related Art

In the past, most researches related to *Clostridium* sp. were about the investigation of the pathogenic strains. Recently, along with the development of biofuels, people paid more attention to the strains of *Clostridium* sp. that are suitable for the production of biofuel. One example of the stains is *Clostridium thermocellum* that has superactive cellulose hydrolase(s) and can directly use cellulose to produce ethanol and hydrogen. Relevant description can be noted from such as "*Appl Environ Microbiol.* 1988 January; 54(1):204-211" by Freier et al., which is entirely incorporated herein by reference. Another example of the strains is *Clostridium ljungdahlii* that is able to use a combination of a carbon oxide (e.g., carbon monoxide, carbon dioxide) and hydrogen as feedstock for producing ethanol.

Although there are various strains useful in the production of biofuels or chemicals, they typically use the saccharide(s) and peptone contained in a fermentation medium as the carbon source and nitrogen source required for the production of organic compounds, and few of them can use different types of substances as the substrate for fermentation. Metabolic products produced from the substrate metabolism of a microorganism through fermentation are normally a mixture with complicated constituents, and thus one or more purification processes are required for obtaining the desired metabolite(s). For example, butanol, ethanol, and acetone as well as minor organic acids (e.g., acetic acid, butyric acid) could be produced by the acetone-butanol-ethanol (ABE) fermentation process of *Clostridium* sp. In addition, the tolerance of microorganism to metabolic products is also an important factor influencing the yield of the fermentation. Accordingly, there is still a need in the industry for a microorganism capable of using different types of substrates and providing an excellent yield of target product at the same time, and thus person in the field have been endeavoring the research and development of strains being able to use various feedstock in the production of chemicals or biofuels and having a high tolerance to the products.

The present invention is directed to the above needs. The inventors of the present invention adaptively selected and obtained a novel strain of *Clostridium cadaveris*, *Clostridium cadaveris* ITRI04005 which is capable of using saccharide(s) and/or amino acid(s) as the substrate to produce an organic compound. Compared with known *Clostridium* strains, *Clostridium cadaveris* ITRI04005 is more suitable for use in a genetic modification to provide a genetically modified strain which is capable of using saccharide(s) and/or amino acid(s) as the substrate to produce an organic acid or an alcohol, has a high specificity of product, and/or has a high tolerance to product. The genetically modified strain can use various feedstock sources to produce chemicals or biofuels, and provides the target product in a good yield.

SUMMARY

An objective of the present invention is to provide an isolated strain of *Clostridium cadaveris*, *Clostridium cadaveris* ITRI04005 which has been deposited at German Collection of Microorganisms and Cell Cultures (Deutsche Sammlung von Mikroorganismen und Zellkulturen GmbH, DSMZ) under the accession number DSM 32078. The *Clostridium cadaveris* ITRI04005 has a 16S rRNA fragment of SEQ ID NO: 1 or a 16S rRNA fragment having at least 95% identity to SEQ ID NO: 1.

Another objective of the present invention is to provide a genetically modified strain obtained from the genetic modification of *Clostridium cadaveris* ITRI04005. Preferably, the genetically modified strain has a 16S rRNA fragment of SEQ ID NO: 1 or a 16S rRNA fragment having at least 95% identity to SEQ ID NO: 1. Preferably, the genetically modified strain meets at least one of the following requirements:

(1) being able to express an exogenous gene or having an endogenous gene with an enhanced expression level, wherein each of the exogenous gene and the endogenous gene is a gene of an enzyme involved in an alcohol production pathway;

(2) having an endogenous gene with an attenuated expression level or without any expression level, wherein the endogenous gene is a gene of an enzyme participating in synthesis of acetic acid; and (3) being able to express an exogenous gene or having an endogenous gene with an enhanced expression level, wherein each of the exogenous gene and the endogenous gene is a gene of a heat shock protein (HSP).

Another objective of the present invention is to provide a method of producing an organic acid. The method comprises providing a substrate, and subjecting the above *Clostridium cadaveris* ITRI04005 and/or genetically modified strain to use the substrate under an anaerobic atmosphere to perform fermentation and to produce an organic acid.

Yet another objective of the present invention is to provide a method of producing an alcohol. The method comprises providing a substrate, and subjecting the above genetically modified strain to use the substrate under an anaerobic atmosphere to perform fermentation and to produce an alcohol, wherein the genetically modified strain is capable of expressing an exogenous gene or has an endogenous gene with an enhanced expression level, wherein each of the exogenous gene and the endogenous gene is a gene of an enzyme involved in an alcohol production pathway.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIGS. 2A and 2B are bar diagrams showing the carbon conversion rates of butyric acid and obtained by incubating *Clostridium cadaveris* ITRI04005 and *Clostridium cadaveris* type strain BCRC 14511 in a medium under an anaerobic atmosphere to perform fermentation, wherein FIG. 2A shows the results of using a CGM medium with a glucose concentration of 5 g/L and FIG. 2B shows the results of using a CGM medium with a glucose concentration of 3 g/L and a lactate concentration of 2 g/L;

FIGS. 7A and 7B are curve diagrams showing the $OD_{600}$ values at different time points and obtained by incubating *Clostridium cadaveris* ITRI04005 and ITRI05023 in a CGM medium with different sodium butyrate concentrations, wherein FIG. 7A shows the results of a CGM medium with 10 g/L of sodium butyrate and FIG. 7B shows the results of a CGM medium with 15 g/L of sodium butyrate.

DESCRIPTION OF THE PREFERRED EMBODIMENT

Figure 1:
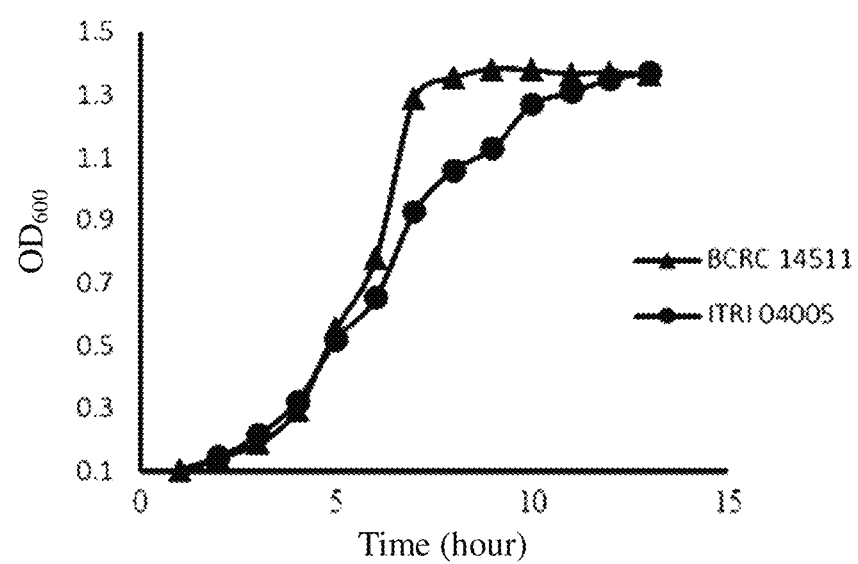
FIG. 1 is a curve diagram showing the $OD_{600}$ values at different time points and obtained by incubating *Clostridium cadaveris* ITRI04005 and the *Clostridium cadaveris* type strain BCRC 14511 in a CGM medium with a glucose concentration of 5 g/L under an anaerobic atmosphere.

The following will describe some of the embodiments of the present invention in detail. However, without departing from the spirit of the present invention, the present invention may be embodied in various embodiments and should not be limited to the embodiments described in the specification. In addition, unless otherwise indicated herein, the expressions "a," "an", "the", or the like recited in the specification of the present invention (especially in the claims) are intended to include the singular and plural forms. Furthermore, the term "about", "approximate", or "almost" used in the specification are substantially represented within ±20% of the stated value, preferably within ±10%, and more preferably within ±5%.

In the present invention, the term "microorganism" refers to an organism that is invisible to naked eyes (e.g., bacteria and fungi) and includes the wild type present in nature and mutant type induced by any factors (e.g., natural factor or artificial factor). The term "fermentation" refers to a process for metabolizing a substrate by a microorganism to produce an organic compound. The term "medium" refers to a composition providing nutrients and conditions (e.g., pH value, humidity, etc.) essential to the growth and replication of a microorganism. In general, the components of the medium would be adjusted in accordance with the type of the microorganism strain to be incubated. For instance, adjustment onto the medium could be made by adding HCl, NaOH, $NH_4OH$, $(NH_4)_2SO_4$, $NH_4Cl$, $CH_3COONH_4$, $K_2HPO_4$, $KH_2PO_4$, $NaH_2PO_3$, $Na_2HPO_3$, citric acid, $MgSO_4 \cdot 7H_2O$, $FeSO_4 \cdot 7H_2O$, or $MnSO_4 \cdot 7H_2O$ so as to provide a medium with a desired pH value (e.g., pH 5.5, pH 6) and/or desired physiochemical or physiological properties. The term "substrate" refers to a material that can be used in the fermentation of a microorganism, and thus, enters the metabolic pathway of the fermentation and then converts into an organic acid. The substrate used in the present invention comprises such as a saccharide, an amino acid, or a combination thereof.

Furthermore, unless specifically indicated, the chemical names recited in the specification include all their isomer forms. Examples of the isomer forms include, but are not limited to, enantiomers, diastereomers and conformational isomers. For instance, the terms "lactic acid", "glucose", "xylose" and "galactose" all include their D-form and L-form isomers. Furthermore, when a saccharide can present in both open ring form and ring form at the same time, the chair form of its conformation isomer and its α, β isomers are all included.

In the specification, the term "carbon conversion rate" of a fermentation refers to the ratio between the total carbon number of the produced organic compound and the total carbon number of the consumed carbon source in the fermentation, and is calculated by Formula 1 as follows:

$$\text{carbon conversion rate} = \frac{\text{the total carbon number of produced organic compound}}{\text{the total carbon number of consumed carbon source}} \times 100\% \quad \text{Formula 1}$$

The inventors of the present invention adaptively selected out a novel *Clostridium* strain from a soil sample, analyzed the strain by 16S rRNA sequencing, and identified the strain as a *Clostridium cadaveris* based on the phylogenetic relationship and named it as *Clostridium cadaveris* ITRI04005. *Clostridium cadaveris* ITRI04005 has been deposited at German Collection of Microorganisms and Cell Cultures (Deutsche Sammlung von Mikroorganismen and Zellkulturen GmbH, DSMZ) under the accession number DSM 32078. The *Clostridium cadaveris* ITRI04005 has a 16S rRNA fragment of SEQ ID NO: 1 or a 16S rRNA fragment having at least 95% identity to SEQ ID NO: 1.

It is noted that, as compared with known *Clostridium* strains, *Clostridium cadaveris* ITRI04005 of the present invention is more suitable for genetic modification. Accordingly, the present invention also relates to a genetically modified strain obtained from the genetic modification of *Clostridium cadaveris* ITRI04005.

In the present invention, the term "genetic modification" refers to the use of a modern molecular biotechnology to artificially modify or change the hereditary substance of a species (e.g., animal, plant, microorganism, and virus). Approaches that can be used in genetic modification include, but are not limited to, gene knock-out, gene deletion, gene silencing, gene attenuation, gene overexpression, etc.

The term "gene knock-out", "gene deletion", or "gene silencing" refers to the modification by such as mutation, substitution, deletion, or addition of one or more nucleotides or an entire gene fragment, to make one or more endogenous genes not be expressed (i.e., blocking the expression of the endogenous gene(s)) and lose the function(s) thereof. The term "gene attenuation" refers to the modification by such as mutation, substitution, deletion, or addition of one or more nucleotides or an entire gene fragment, to make the expression level of one or more endogenous genes decreased (i.e., partially blocking the expression of the endogenous gene(s) or the essential part(s) thereof). The term "gene overexpression" refers to the modification by such as the mutation, substitution, deletion, or addition of one or more nucleotides or an entire gene fragment, to render one or more exogenous genes to express or to enhance the expression level of one or more endogenous genes.

Preferably, the strain obtained from the genetic modification of *Clostridium cadaveris* ITRI04005 and according to the present invention meets at least one of the following requirements: (1) being able to express an exogenous gene or having an endogenous gene with an enhanced expression level, wherein each of the exogenous gene and the endogenous gene is a gene of an enzyme involved in an alcohol production pathway; (2) having an endogenous gene with an attenuated expression level or without any expression level, wherein the endogenous gene is a gene of an enzyme participating in synthesis of acetic acid; and (3) being able to express an exogenous gene or having an endogenous gene with an enhanced expression level, wherein each of the exogenous gene and the endogenous gene is a gene of a heat shock protein (HSP). Examples of the gene of an enzyme involved in the alcohol production pathway include, but are not limited to, alcohol dehydrogenase (adh), aldehyde dehydrogenase (ald), aldehyde/alcohol dehydrogenase (aad), and butanol dehydrogenase (bdh); examples of the gene of an enzyme participating in the synthesis of acetic acid include, but are not limited to, phosphate acetyltransferase (pta) and acetate kinase (ack); and examples of the gene of a heat shock protein (HSP) include, but are not limited to, heat shock protein 18 (hsp18) and groESL.

Preferably, the genetically modified strain according to the present invention has a 16S rRNA fragment of SEQ ID NO: 1 or a 16S rRNA fragment having at least 95% identity to SEQ ID NO: 1.

It has been found that both the *Clostridium cadaveris* ITRI04005 and the genetically modified strain meeting the above requirement (2) and/or requirement (3) according to the present invention are all capable of producing an organic acid. Therefore, the present invention also provides a method of producing an organic acid and the method comprises: providing a substrate; and subjecting the *Clostridium cadaveris* ITRI04005 and/or the genetically modified strain to use the substrate under an anaerobic atmosphere to perform fermentation. Preferably, the organic acid thus produced is a C1-C4 organic acid such as acetic acid, propionic acid, butyric acid, lactic acid, and a combination thereof. In one embodiment of the present invention, the organic acid is mainly butyric acid.

As shown in the examples below, as compared with the organic acid product obtained by using a non-modified wild type strain in a substrate under an anaerobic atmosphere to perform fermentation, the organic acid product obtained by using a genetically modified strain according to the present invention has a higher butyric acid/acetic acid weight ratio (i.e., B/A ratio), wherein the genetically modified strain has an endogenous gene with an attenuated expression level or without any expression level and the endogenous gene is a gene of an enzyme participating in synthesis of acetic acid. Specifically, in the organic acid product obtained from the use of the genetically modified strain, the B/A ratio is more than 10.

On the other hand, it has also been found that the genetically modified strain being able to express an exogenous gene or having an endogenous gene with an enhanced expression level according to the present invention, wherein each of the exogenous gene and the endogenous gene is a gene of an enzyme involved in an alcohol production pathway, can further convert an organic acid into an alcohol. Therefore, the present invention also provides a method of producing an alcohol and the method comprises: providing a substrate; and subjecting the genetically modified strain to use the substrate under an anaerobic atmosphere to perform fermentation and produce an alcohol. Preferably, the alcohol thus produced is ethanol, isopropanol, and/or butanol. In one embodiment of the present invention, the alcohol is mainly butanol.

In the method of producing an organic acid or an alcohol according to the present invention, the term "anaerobic atmosphere" refers to an atmosphere that contains less than 5 ppm (part per million) of oxygen, preferably less than 0.5 ppm of oxygen, and more preferably less than 0.1 ppm of oxygen. Any suitable method can be used to provide the desired anaerobic atmosphere. For example, but is not limited to, before the fermentation is performed, an inert gas (e.g., nitrogen, carbon dioxide) is introduced into the fermentation reactor to purge the reactor, and thus, provide the desired anaerobic atmosphere; alternatively, the fermentation is performed in an anaerobic operation box, wherein a palladium catalyst is used to catalyze the reaction of the oxygen in the box and the hydrogen in the anaerobic gas mixture to produce water, and thus, provide the desired anaerobic atmosphere.

Furthermore, in the method of producing an organic acid or an alcohol according to the present invention, the substrate for the fermentation comprises a saccharide, an amino acid, or a combination thereof; preferably, the substrate comprises at least an amino acid; and more preferably, the substrate comprises a saccharide and an amino acid.

Examples of the saccharide suitable for the substrate in the method of the present invention include, but are not limited to, a monosaccharide (e.g., glucose, fructose, galactose, mannose, arabinose, lyxose, ribose, xylose, ribulose, xylulose, allose, altrose, gulose, idose, talose, psicose, sorbose, tagatose); a disaccharide (e.g., sucrose, maltose, lactose, lactulose, trehalose, cellobiose); an oligosaccharide (e.g., stachyose, maltotriose, maltotetrose, maltopentaose); and a polysaccharide (e.g., starch, cellulose, glycogen, cyclodextrin, arabinoxylans, guar gum, gum arabic, chitin, gum, alginate, pectin, gellan). In one embodiment of the present invention, a glucose-containing substrate was used as the carbon source needed in the fermentation.

In the process of the growth and replication of a microorganism, amino acid is typically served as a nitrogen source needed for protein synthesis. However, different from such use, in the method of producing an organic acid or an alcohol according to the present invention, an amino acid-containing substrate is used as a carbon source needed in the fermentation. Suitable amino acid sources include such as yeast extract, protein hydrolysate, peptone, corn steep liquor, whey, soybean meal, fish meal, meat bone meal, yeast powder, and soybean powder, but are not limited thereby. In one embodiment of the present invention, a peptone-containing substrate was used to provide the carbon source needed in the fermentation.

In the method of producing an organic acid or an alcohol of the present invention, there is no particular limitation to the order of mixing the substrate and the strain. The substrate can be added at one time or in several batches before or during the fermentation, and the strain can be supplemented optionally. For instance, the substrate can be mixed with the strain at one time before performing the fermentation; the substrate also can be divided into two or more equal or unequal batches, and then the batches are separately added into the reactor before or during the fermentation.

Optionally, before the method of producing an organic acid or an alcohol according to the present invention starts, the *Clostridium cadaveris* ITRI04005 and/or the genetically modified strains of the present invention can be pre-cultured until they grow into the log phase. And such pre-cultured strains are used to perform fermentation to produce the desired organic acid or alcohol.

The present invention will be further illustrated in detail with specific examples as follows. However, the following examples are provided only for illustrating the present invention, and the scope of the present invention is not limited thereby.

EXAMPLES

The materials used in the following examples comprise components as follows:
(a) CGM (Clostridial Growth Medium) medium (yeast extract: 5 g/L; peptone: 5 g/L; $(NH_4)_2SO_4$: 3 g/L; $K_2HPO_4$: 1.5 g/L; $MgSO_4 \cdot 7H_2O$: 0.6 g/L; $FeSO_4 \cdot 7H_2O$: 0.03 g/L; pH6.8).
(b) RCM (Reinforced Clostridial Medium) medium (meat extract: 10 g/L; peptone: 10 g/L; yeast extract: 3 g/L; D-(+)-glucose: 10 g/L; NaCl: 5 g/L; sodium acetate: 3 g/L; L-cysteine hydrochloride: 0.5 g/L; starch: 1 g/L; agar: 0.5 g/L; pH6.0).
(c) P2 medium (yeast extract: 5 g/L; $C_2H_3O_2NH_4$: 2.2 g/L; $MnSO_4 \cdot 7H_2O$: 0.01 g/L; NaCl: 1 g/L; $MgSO_4 \cdot 7H_2O$: 0.2 g/L; $FeSO_4 \cdot 7H_2O$: 0.01 g/L; $KH_2PO_4$: 0.75 g/L; $K_2HPO_4$: 0.75 g/L; p-amino benzoic acid (PABA): 0.001 g/L; biotin: 0.0001 g/L; pH6.0).

In the following examples, an anaerobic atmosphere was provided in an air-tight container (e.g., air-tight bottle, centrifuge tube) by the following operations. The air-tight container and the rubber bung were covered with aluminum foil, and then sterilized under high temperature and high pressure (121° C., 1.2 atm) to exclude the interference of other microorganisms. After the sterilization was completed, the air-tight container was put in an oven to remove the residual moisture to prevent any microorganism contamination caused by the residual moisture. Thereafter, the dried air-tight container was transferred to an anaerobic operation box through the transfer box appended to the anaerobic operation box. After the sealing aluminum foil was slightly loosened, the palladium catalyst (purchased from Thermo Scientific, Inc., product number: BR0042) appended to the anaerobic operation apparatus was used to catalyze the reaction of the oxygen in the air-tight container and the hydrogen in the anaerobic gas mixture to produce water and to deplete the oxygen in the air-tight container, and thus, provide an anaerobic atmosphere.

In the following examples, all the mediums were treated as follows to be deoxygenated. First of all, the medium was prepared with desired composition. The prepared medium was sterilized under high temperature and high pressure (121° C., 1.2 atm), and then transferred into an anaerobic operation box through the transfer box appended to the anaerobic operation box before the medium cooled down to room temperature. Thereafter, the cap of the air-tight container in which the medium was kept was slightly loosened to release the steam contained therein. Then, with the use of the palladium catalyst appended to the anaerobic operation apparatus, the reaction of the oxygen in the air-tight container and the hydrogen in the anaerobic gas mixture was catalyzed to produce water such that a deoxygenated medium was provided.

Example 1: Adaptive Selection of Novel Strain(s)

(1-1) Method for Adaptive Selection

A soil sample was obtained and sealed in a serum bottle that contained 50 ml of sterile water. The serum bottle was placed in a water bath at 70° C. for 10 minutes and then taken out therefrom. After the serum bottle was cooled down to room temperature, a saccharide-free CGM medium containing two times of desired component concentrations was added into the serum bottle at a volume equal to the sample. Thereafter, a sterilized solution of L-cysteine HCl was added into the serum bottle at a final concentration of 0.005% (weight/volume) to deplete the residual oxygen and to accelerate the growth of the strains contained therein.

The above deoxygenated sample was placed in an anaerobic incubator at 37° C. for observation. Once the production of gas started, the types of the strains contained in the sample were analyzed with the use of PCR (polymerase chain reaction) in combination with the specific primers shown in Table 1. Among the tabulated primers, the EuB 968F/Univer 1392R primer pair could widely detect whether the sample contained any bacteria, and the Clo16S-deg F1/Clo16S-deg-R1 primer pair could detect whether the sample contained any *Clostridium* sp. bacteria.

Once confirmed that the sample contained *Clostridium* sp. bacteria, the sample was well mixed and then diluted serially by a micropipet to provide diluted solutions of 10,000-fold dilution, 100,000-fold dilution, and 1,000,000-fold dilution, respectively. Each of the diluted solutions was spread onto an individual saccharide-free CGM agar plate (a saccharide free-CGM medium added with 15 g/L of agar) and incubated in an anaerobic incubator at 37° C. until single colony appeared. Thereafter, to confirm the uniqueness of the selected strain, each of the single colonies with different morphology was sampled with the use of a sterilized inoculating loop and subjected to the four-quarter steaking method on a RCM agar plate (a RCM medium added with 15 g/L of agar). Then, the RCM agar plates were incubated in an anaerobic incubator at 37° C. until single colony appeared.

Through the above adaptive selection with the use of a saccharide-free selective medium, the *Clostridium* sp. capable of using a non-saccharide substrate as the carbon source for growth could be adaptively selected. On the other hand, since the main component of the above saccharide-free selective medium was protein hydrolysate or amino acid(s), strain(s) capable of using an amino acid as a carbon source for growth could be adaptively selected.

TABLE 1

| Primer name | Nucleotide sequence of primer | Sequence number |
|---|---|---|
| EuB 968F | 5'-AACGCGAAGAACCTTAC-3' | SEQ ID NO: 2 |
| Univer 1392R | 5'-ACGGGGGGTGTGTAC-3' | SEQ ID NO: 3 |
| Clo16S-deg F1 | 5'-GCGGCGTGCYTAAYACATGC-3' | SEQ ID NO: 4 |
| Clo16S-deg-R1 | 5'-GGGTTGCGCTCGTTGCRGGA-3' | SEQ ID NO: 5 |

(1-2) Identification of Strain(s)

Phylogenetic analysis was conducted on the strain adaptively selected from experiment (1-1), and it was confirmed that the strain had a 16S rRNA fragment of SEQ ID NO: 1. As a result of the comparison with the online database of National Center for Biotechnology Information, it was noted that SEQ ID NO:1 had an identity of about 99% to the 16S rRNA fragment of *Clostridium cadaveris* strain. Hence, the strain was identified as a *Clostridium cadaveris* strain according to the phylogenetic relationship and named as *Clostridium cadaveris* ITRI04005.

The appearance of *Clostridium cadaveris* ITRI04005 was observed by naked eyes and was present as a smooth-surrounding colony with gloss and in earthy yellow color. The morphology of *Clostridium cadaveris* ITRI04005 was further observed under a microscope, revealing a *bacillus* having motility and being able to produce spindle-shaped endospores on its both sides.

(1-3) Physiological Properties Analysis of *Clostridium cadaveris* ITRI04005

(1-3-1) Growth Rate (A) Pre-Culture

Each of the single colonies of *Clostridium cadaveris* ITRI04005 and *Clostridium cadaveris* type strain BCRC14511 was inoculated into 10 ml of deoxygenated RCM medium, and incubated in an anaerobic incubator at 37° C. for about 12 to 14 hours so as to enter the mid-log growth phase (i.e., the $OD_{600}$ (the absorbance at a wavelength of 600 nm) of the strain reached about 1.0 to 1.2).

(B) Measurement of Growth Curves

CGM medium was mixed with glucose to provide a medium mixture with a glucose concentration of 5 g/L (pH=6.0), and then the medium mixture was deoxygenated.

Each of two air-tight bottles was injected with 100 ml of the deoxygenated medium mixture, and one bottle was inoculated with the pre-cultured *Clostridium cadaveris* ITRI04005 and the other was inoculated with the pre-cultured *Clostridium cadaveris* type strain BCRC14511, wherein the initial concentration of strain in the medium mixture of each bottle was adjusted such that the $OD_{600}$ of the medium was about 0.1. Then, the bottles were kept in an anaerobic incubator at 37° C. and samples were taken therefrom at scheduled time points to measure the $OD_{600}$ thereof. The results are shown in FIG. 1.

As shown in FIG. 1, *Clostridium cadaveris* ITRI04005 and *Clostridium cadaveris* type strain BCRC14511, as being incubated in a medium mixture with a glucose concentration of 5 g/L, had different growth rates. This result indicates that *Clostridium cadaveris* ITRI04005 and *Clostridium cadaveris* type strain BCRC14511 are different strains.

(1-3-2) Substrate Utilization and Products

Different medium mixtures with a carbon source concentration of 5 g/L were prepared by mixing CGM medium with each of the carbon sources tabulated in Table 2, and were deoxygenated. Thereafter, each of the deoxygenated medium mixtures was used as follows. 40 ml of the deoxygenated medium mixture was injected into a 50 ml centrifuge tube, and then was inoculated with *Clostridium cadaveris* ITRI04005 and kept in an anaerobic incubator at 37° C. for 24 hours. Samples were taken from the inoculated medium mixture and were centrifuged (0° C., 12,000 g, 5 minutes; the centrifuge was purchased from Kubota Co.), and the strains contained therein were removed with the use of a 0.22 μm filter. The components of the supernatant thus obtained were analyzed by Agilent 1100 high performance liquid chromatography (HPLC) analysis in combination with Aminex HPX-87H (300×7.8 mm) column, and the amounts of butyric acid and total products were determined. The results are shown in Table 2.

As shown in Table 2, even though the culture medium of *Clostridium cadaveris* ITRI04005 was only added with a substrate containing yeast extract and protein hydrolysate, there was butyric acid in the supernatant. This result indicates that, in the absence of saccharide, *Clostridium cadaveris* ITRI04005 can use an amino acid as a substrate to perform fermentation and convert the amino acid into products such as butyric acid.

TABLE 2

| | Concentration of product (g/L) | |
|---|---|---|
| Carbon source | Butyric acid | Total products |
| 1. Glucose | 2.05 | 2.64 |
| 2. Glucose + lactic acid | 3.26 | 3.92 |
| 3. Fructose | 1.02 | 1.73 |
| 4. Arabinose | 0.34 | 0.90 |
| 5. Xylose | 0.35 | 0.91 |
| 6. Cellobiose | 0.50 | 1.23 |
| 7. Sucrose | 0.50 | 1.32 |
| 8. Starch | 0.79 | ND |
| 9. Cellulose | 0.00 | 0.04 |
| 10. Glycerol | 0.52 | 1.43 |
| 11. Carboxymethyl cellulose | 0.95 | ND |
| 12. Yeast extract + protein hydrolysate | 0.68 | 1.59 |

(1-4) Comparison of *Clostridium cadaveris* ITRI04005 and *Clostridium Cadaveris* Type Strain BCRC14511

(1-4-1) Carbon Conversion Rate Comparison (A) Pre-Culture

Each of the single colonies of *Clostridium cadaveris* ITRI04005 and *Clostridium cadaveris* type strain BCRC14511 was inoculated into 10 ml of deoxygenated RCM medium, and was incubated in an anaerobic incubator at 37° C. for about 12 to 14 hours so as to enter the mid-log growth phase (i.e., the $OD_{600}$ reached about 1.0 to 1.2).

(B) Performing Fermentation

CGM medium was mixed with glucose to provide a medium mixture with a glucose concentration of 5 g/L (pH=6.0). The medium mixture was mixed with a 20 mM MES buffer (purchased from Sigma-Aldrich) to adjust its pH value, and then was deoxygenated.

Figure 2A:
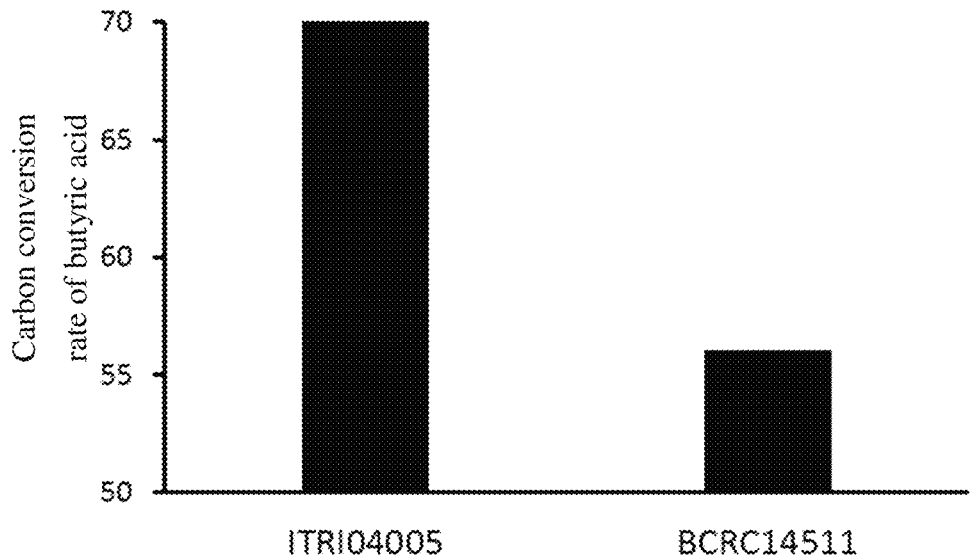

Each of two 50 ml centrifuge tubes was injected with 40 ml of the deoxygenated medium mixture, and then one was inoculated with the pre-cultured *Clostridium cadaveris* ITRI04005 and the other was inoculated with the pre-cultured *Clostridium cadaveris* type strain BCRC14511 and both were at 5% inoculation rate. Thereafter, the two tubes were kept in an anaerobic incubator at 37° C. Samples were taken from the two tubes as the strains grew to reach an $OD_{600}$ of about 1.4, and then were analyzed by Agilent 1100 HPLC analysis in combination with Aminex HPX-87H (300×7.8 mm) column so as to calculate the consumption of glucose and the yield of butyric acid in the culture medium. The results are shown in Table 3. In addition, the carbon conversion rates were calculated by Formula 2, and the results are shown in Table 3 and FIG. 2A.

$$\frac{\frac{\text{yield of butyric acid}}{\text{molecular weight of butyric acid}} \times 4}{\frac{\text{consumption of glucose}}{\text{molecular weight of glucose}} \times 6} \times 100\% \quad \text{Formula 2}$$

TABLE 3

|  | Consumption of glucose (g/L) | Yield of butyric acid (g/L) | Carbon conversion rate of butyric acid (%) |
| --- | --- | --- | --- |
| *Clostridium cadaveris* ITRI04005 | 2.51 | 1.28 | 70% |
| *Clostridium cadaveris* type strain BCRC14511 | 2.12 | 0.87 | 56% |

As shown in Table 3 and FIG. 2, in a glucose-containing CGM medium, the carbon conversion rate of butyric acid provided by *Clostridium cadaveris* ITRI04005 was about 70%, and that by *Clostridium cadaveris* type strain BCRC14511 was about 56%. These results indicate that *Clostridium cadaveris* ITRI04005 of the present invention could provide a better carbon conversion rate than *Clostridium cadaveris* type strain BCRC14511.

(1-4-2) Comparison of Abilities to Metabolize Substrate (A) Pre-Culture

Each of the single colonies of *Clostridium cadaveris* ITRI04005 and *Clostridium cadaveris* type strain BCRC14511 was inoculated into 10 ml of the deoxygenated RCM medium, and was incubated in an anaerobic incubator at 37° C. for about 12 to 14 hours so as to enter the mid-log growth phase (i.e., the $OD_{600}$ reached about 1.0 to 1.2).

(B) Performing Fermentation

CGM medium was mixed with glucose and lactate to provide a medium mixture with a glucose concentration of 3 g/L and a lactate concentration of 2 g/L (pH6.0). The medium mixture was mixed with a 20 mM MES buffer to adjust its pH value, and then was deoxygenated.

Each of two 50 ml centrifuge tubes was injected with 40 ml of the deoxygenated medium mixture, and then one was inoculated with the pre-cultured *Clostridium cadaveris* ITRI04005 and the other was inoculated with the pre-cultured *Clostridium cadaveris* type strain BCRC14511 and both were at 5% inoculation rate. Thereafter, the two tubes were kept in an anaerobic incubator at 37° C. for 11 hours. Samples were taken from the tubes and analyzed by Agilent 1100 HPLC analysis in combination with Aminex HPX-87H (300×7.8 mm) column so as to calculate the consumption of glucose and lactic acid and the yield of butyric acid in the culture medium. The results are shown in Table 4. In addition, the carbon conversion rates were calculated by Formula 3, and the results are shown in Table 4 and FIG. 2B.

$$\frac{\frac{\text{yield of butyric acid}}{\text{molecular weight of butyric acid}} \times 4}{\frac{\text{consumption of glucose}}{\text{molecular weight of glucose}} \times 6 + \frac{\text{consumption of lactic acid}}{\text{molecular weight of lactic acid}} \times 3} \times 100\% \quad \text{Formula 3}$$

TABLE 4

|  | Consumption of glucose (g/L) | Consumption of lactic acid (g/L) | Yield of butyric acid (g/L) | Carbon conversion rate of butyric acid (%) |
| --- | --- | --- | --- | --- |
| *Clostridium cadaveris* ITRI04005 | 2.6 | 1.1 | 1.7 | 65% |
| *Clostridium cadaveris* type strain BCRC14511 | 2.5 | 0.5 | 1.3 | 55% |

Figure 2B:
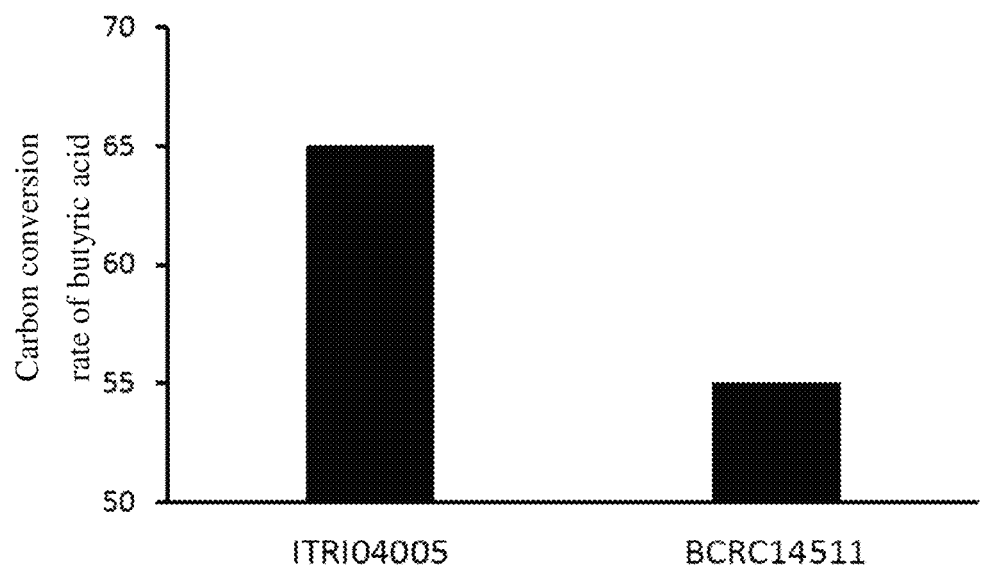

As shown in Table 4 and FIG. 2B, under the same cultivation conditions, *Clostridium cadaveris* type strain BCRC14511 only metabolized about 0.5 g/L of lactic acid and *Clostridium cadaveris* ITRI04005 metabolized about 1.1 g/L of lactic acid. On the other hand, under the conditions that both glucose and lactic acid were present, the carbon conversion rate of butyric acid provided by *Clostridium cadaveris* ITRI04005 was about 65% and that by *Clostridium cadaveris* type strain BCRC14511 was about 55%. These results indicate that, as compared with *Clostridium cadaveris* type strain BCRC14511, *Clostridium cadaveris* ITRI04005 of the present invention has a better lactic acid metabolism ability, and thus, could provide a better carbon conversion rate.

Example 2: Preparation of Genetically Modified Strains (2-1) Genetically Modified Strain "being Able to Express an Exogenous Gene or Having an Endogenous Gene with an Enhanced Expression Level, Wherein Each of the Exogenous Gene and the Endogenous Gene is a Gene of an Enzyme Involved in an Alcohol Production Pathway"

(2-1-1) Plasmid Cloning and Verification

Figure 3:
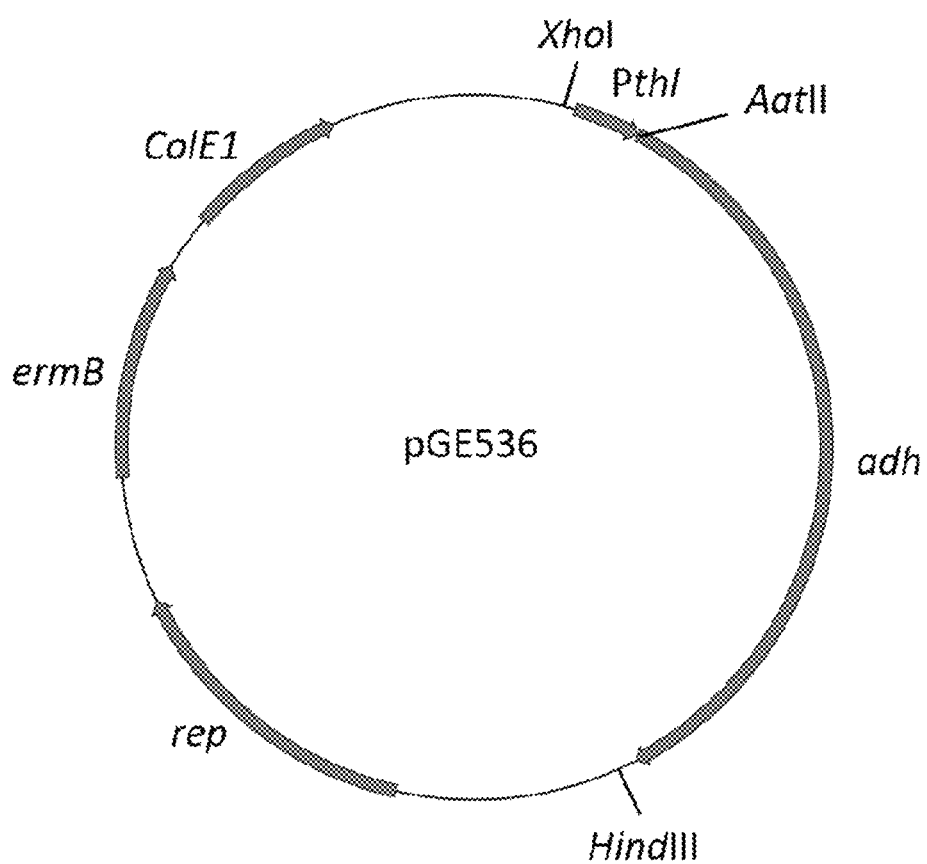
FIG. 3 illustrates pGE536 recombinant plasmid carrying alcohol dehydrogenase (adh)

A pGE536 recombinant plasmid which carries adh gene was prepared by amplifying alcohol dehydrogenase (adh) (its gene source was *Clostridium acetobutylicum* ATCC 824) with the use of PCR in combination with the specific primers as shown in the Table 5 (i.e., #232 and #233) and cloning the amplified adh gene into a shuttle vector of *Clostridium* sp. (as shown in FIG. 3). Then, the pGE536 plasmid was transformed into *Clostridium cadaveris* ITRI04005 by the electroporation genetic transformation technology (each pulse: voltage (2.5 kV); resistance (600Ω); capacity (25 µF)) to provide a genetically modified strain. Thereafter, an erythromycin-containing RCM medium was used to select the genetically modified strain; if a strain could survive in the aforementioned medium, it might carry the pGE536 recombinant plasmid.

The strain thus selected was incubated in an erythromycin-containing RCM medium, and its plasmid DNA was extracted. Thereafter, a fragment of erythromycin resistance gene (ermb) and a fragment of alcohol dehydrogenase (adh) in the extracted plasmid DNA were amplified with the use of PCR in combination with the specific primers as shown in Table 5 (the specific primers for ermb gene were #164 and #165, and the specific primers for adh gene were #45 and #284), and an agarose gel electrophoresis was conducted on each of the amplified fragments to confirm whether a PCR product with specificity had been produced.

Through the above plasmid DNA extraction and the PCR in combination with the specific primer, it was confirmed that the selected strain carried the pGE536 plasmid. That is, the genetically modified strain indeed carried adh gene (i.e., the genetically modified strain was able to express an exogenous gene or having an endogenous gene with an enhanced expression level, wherein each of the exogenous gene and the endogenous gene is a gene of an enzyme involved in an alcohol production pathway), and was named as *Clostridium cadaveris* ITRI05007.

TABLE 5

| Primer name | Nucleotide sequence of the primer | Sequence number |
|---|---|---|
| #232 | 5'-GCGACGTCATGAAAGTTACAAATCAAA AAGAAC-3' | SEQ ID NO: 6 |
| #233 | 5'-CGGGATTCATAATGAAGCAAAGACTAT TTTAC-3' | SEQ ID NO: 7 |
| #164 | 5'-CTTTAATAGTTTGTGGTT-3' | SEQ ID NO: 8 |
| #165 | 5'-TTATTTCCTCCCGTTAAA-3' | SEQ ID NO: 9 |
| #45 | 5'-GTAAAACGACGGCCAGTG-3' | SEQ ID NO: 10 |
| #284 | 5'-GAAGCAGAAATTGAAAATCTAGC-3' | SEQ ID NO: 11 |

(2-1-2) Test of the Efficiency of the Genetically Modified Strain in Producing Butyric Acid (A) Pre-Culture RCM medium was mixed with erythromycin and glucose to provide a medium mixture with an erythromycin concentration of 40 µg/ml and a glucose concentration of 10 g/L, and the medium mixture was deoxygenated. Thereafter, each of two 50 ml centrifuge tubes was injected with 20 ml of the deoxygenated medium mixture. One of the two tubes was inoculated with *Clostridium cadaveris* ITRI04005 (hereinafter referred to as "control group" carrying a vector which does not carry the adh gene) and the other was inoculated with ITRI05007 (carrying the pGE536 plasmid), and both tubes were kept in an anaerobic incubator at 37° C. for about 16 to 18 hours so that the stains inoculated therein entered the late-log growth phase or early-lag growth phase (i.e., the $OD_{600}$ reached about 1.6 to 2.0).

(B) Preparation of Medium Mixtures

A medium mixture with a glucose concentration of 10 g/L was prepared by mixing P2 medium with glucose, and then was deoxygenated. Another medium mixture with a glucose concentration of 10 g/L and a peptone concentration of 5 g/L was prepared by mixing glucose, peptone, and P2 medium, and then was deoxygenated as well.

(C) Substrate Utilization and Products

Each of two air-tight bottles was injected with 50 ml of the deoxygenated medium mixture with a glucose concentration of 10 g/L, and then one was inoculated with the pre-cultured *Clostridium cadaveris* ITRI04005 and the other was inoculated with the pre-cultured *Clostridium cadaveris* ITRI05007. The two bottles were kept in an anaerobic incubator at 37° C. and samples were taken therefrom at 0 hour and 15 hours, respectively. The samples were centrifuged (0° C., 12,000 g, 5 minutes; the centrifuge was purchased from Kubota Co.) and the strains contained therein were removed with the use of a 0.22 µm filter. The components of each of thus obtained supernatants were analyzed by Agilent 1100 HPLC analysis in combination with Aminex HPX-87H (300×7 8 mm) column, and the amounts of glucose, acetic acid, butyric acid, and butanol were determined. All of the results are shown in Table 6. The above steps were repeated, but in the deoxygenated medium mixture with a glucose concentration of 10 g/L and a peptone concentration of 5 g/L. The results are shown in Table 7.

As shown in Table 6, the yield of butanol obtained from incubating *Clostridium cadaveris* ITRI04005 or *Clostridium cadaveris* ITRI05007 in a medium being added with only glucose for about 15 hours was 0 g/L or 1.1 g/L. These results indicate that, as compared with *Clostridium cadaveris* ITRI04005 which could not use glucose as the substrate in fermentation to produce butanol, *Clostridium cadaveris* ITRI05007 of the present invention can use glucose to perform fermentation to produce butanol effectively.

On the other hand, as shown in Table 7, the yield of butanol obtained from incubating *Clostridium cadaveris* ITRI05007 in a medium added with both glucose and peptone for about 15 hours was about 2.5 g/L. This result indicates that in addition to glucose, *Clostridium cadaveris* ITRI05007 could use an amino acid as the substrate in fermentation, and thus, could produce more butanol and provide a better yield of butanol.

TABLE 6

| | Substrate/product | | | | | | | |
|---|---|---|---|---|---|---|---|---|
| | Glucose (g/L) | | Acetic acid (g/L) | | Butyric acid (g/L) | | Butanol (g/L) | |
| | Time (hour) | | | | | | | |
| | 0 | 15 | 0 | 15 | 0 | 15 | 0 | 15 |
| ITRI04005 | 10.8 ± 0 | 6.6 ± 0.2 | 2 ± 0 | 2.3 ± 0 | 0.1 ± 0 | 2.5 ± 0.1 | 0 ± 0 | 0 ± 0 |
| ITRI05007 | 10.5 ± 0.1 | 5.7 ± 0.1 | 2 ± 0 | 3 ± 0 | 0.1 ± 0 | 0.9 ± 0 | 0 ± 0 | 1.1 ± 0 |

TABLE 7

| | Substrate/product | | | | | | | |
|---|---|---|---|---|---|---|---|---|
| | Glucose (g/L) | | Acetic acid (g/L) | | Butyric acid (g/L) | | Butanol (g/L) | |
| | Time (hour) | | | | | | | |
| | 0 | 15 | 0 | 15 | 0 | 15 | 0 | 15 |
| ITRI04005 | 10 ± 0.1 | 1.5 ± 0.2 | 2 ± 0 | 2.3 ± 0 | 0.3 ± 0 | 5.1 ± 0.1 | 0 ± 0 | 0 ± 0 |
| ITRI05007 | 10 ± 0.1 | 0 ± 0 | 2 ± 0 | 3.8 ± 0.1 | 0.2 ± 0 | 1.3 ± 0.1 | 0 ± 0 | 2.5 ± 0.1 |

(2-2) Genetically Modified Strain "Having an Endogenous Gene with an Attenuated Expression Level or without any Expression Level, Wherein the Endogenous Gene is a Gene of an Enzyme Participating in Synthesis of Acetic Acid"

(2-2-1) Plasmid Cloning and Verification

Figure 4:
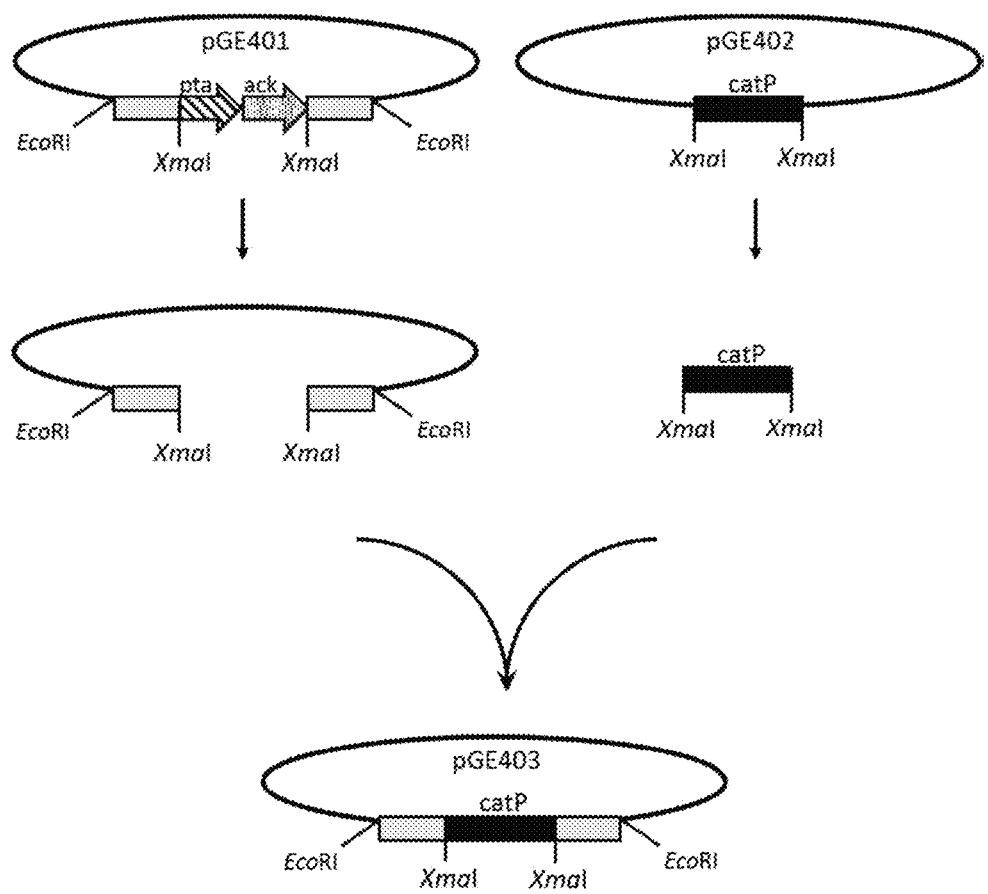
FIG. 4 illustrates the pGE403 transgenic plasmid whose "pta-ack" gene fragment was replaced with a "catP" gene fragment.

The DNA fragment from 1270 base pairs (bp) upstream to phosphate acetyltransferase (pta) to 1263 by downstream to acetate kinase (ack) (hereinafter abbreviated to "pta-ack" fragment) in the genomic DNA of Clostridium cadaveris ITRI04005 was amplified by PCR in combination with the specific primers as shown in Table 8 (i.e., #338 and #339), and then an agarose gel electrophoresis was conducted to purify and isolate the amplified "pta-ack" fragment. In addition, the DNA fragment of Chloramphenicol resistance gene (catP) (hereinafter abbreviated to "catP" fragment) was amplified by PCR in combination with the primers of XmaI restriction site as shown in Table 8 (i.e., #340; #211), and then the agarose gel electrophoresis was conducted to purify and isolate the amplified "catP" fragment. Thereafter, the amplified "pta-ack" fragment and "catP" fragment were cloned into pCR2.1 vector to obtain plasmid pGE401 and plasmid pGE402 respectively, and then the enzyme digestion and ligation of gene fragment were conducted by a restriction enzyme (i.e., XmaI) to obtain a suicide plasmid pGE403 for pta-ack gene knock-out (as shown in FIG. 4).

The plasmid pGE403 was transformed into Clostridium cadaveris ITRI04005 by the electroporation genetic transformation technology (each pulse: voltage (2.5 kV); resistance (600Ω); capacity (25 μF)), and then a catP gene was inserted into the genome of Clostridium cadaveris ITRI04005 to replace the pta-ack gene therein through homologous recombination so as to perform the pta-ack gene knock-out. Thereafter, the strain being resistant to thiamphenicol was selected out with the use of a RCM medium that contained thiamphenicol at a concentration of 5 μg/ml. The strain thus selected was verified by Southern hybridization to confirm that the pta-ack gene in the genome of the strain had been replaced by a catP gene (i.e., the pta-ack gene knock-out procedure had been completed).

By way of the above Southern hybridization, it was confirmed that the pta-ack gene in the genome of the strain had been replaced by a catP gene. That is, the pta and ack genes of the genetically modified strain had indeed been knocked-out (i.e., the genetically modified strain had an endogenous gene with an attenuated expression level or without any expression level, wherein the endogenous gene was a gene of an enzyme participating in synthesis of acetic acid). The genetically modified strain was named as Clostridium cadaveris ITRI05027.

TABLE 8

| Primer name | Nucleotide sequence of the primer | Sequence number |
|---|---|---|
| #338 | 5'-TATGGCAGCACCTTTAGAGT-3' | SEQ ID NO: 12 |
| #339 | 5'-ATTATAGGGGCTAAAGCTGG-3' | SEQ ID NO: 13 |
| #340 | 5'-CCCGGGTGATTGTTATGGATTAT AAG-3' | SEQ ID NO: 14 |
| #211 | 5'-CCCGGGTTAACTATTTATCAATTCC-3' | SEQ ID NO: 15 |

(2-2-2) Test of the Specificity of Fermentation Product of the Genetically Modified Strain (A) Pre-Culture A RCM-Tm medium mixture was prepared by mixing a RCM medium and 5 μg/ml thiamphenicol. Both the remaining RCM medium and the RCM-Tm medium mixture were deoxygenated. Thereafter, one 50 ml centrifuge tubes was injected with 30 ml of the deoxygenated RCM medium and inoculated therein Clostridium cadaveris ITRI04005, and another 50 ml centrifuge tube was injected with 30 ml of the deoxygenated RCM-Tm medium mixture and inoculated therein Clostridium cadaveris ITRI05027. Both tubes were kept in an anaerobic incubator at 37° C. for about 16 to 18 hours such that the strains contained therein entered the late-log growth phase or early-lag growth phase (i.e., the OD$_{600}$ reached about 1.6 to 2.0).

(B) Preparation of Medium Mixtures

CGM medium was mixed with glucose to provide a CGM medium mixture with a glucose concentration of 10 g/L. In addition, CGM medium was mixed with glucose and thiamphenicol to provide a CGM-Tm medium mixture with a glucose concentration of 10 g/L and a thiamphenicol concentration of 5 μg/ml. Both the two medium mixtures were deoxygenated.

(C) Test of the Specificity of Fermentation Products

One 50 ml centrifuge tube was injected with 30 ml of the deoxygenated CGM medium mixture and inoculated therein Clostridium cadaveris ITRI04005, and another 50 centrifuge tube was injected with 30 ml of the deoxygenated CGM-Tm medium mixture and inoculated therein Clostridium cadaveris ITRI05027. Both tubes were kept in an anaerobic incubator at 37° C. for about 48 hours. Samples were taken from the two tubes in a sterile operation bench, and then centrifuged (0° C., 12,000 g, 5 minutes, the centrifuge was purchased from Kubota Co.) Strains contained in each sample were removed with the use of a 0.22 μm filter, and the components of the supernatant were analyzed by Agilent 1100 HPLC analysis in combination with Aminex HPX-87H (300×7.8 mm) column so as to calculate the consumption of glucose and the yields of acetic acid and butyric acid. The butyric acid/acetic acid ratio (B/A ratio) was also calculated. All of the results are shown in Table 9.

As shown in Table 9, the B/A ratio obtained by performing fermentation with the use of Clostridium cadaveris ITRI05027 was higher than that with the use of Clostridium cadaveris ITRI04005. This result indicate that as compared with Clostridium cadaveris ITRI04005, Clostridium cadaveris ITRI05027 had a better specificity of the fermentation products.

TABLE 9

| | Consumption of glucose (g/L) | Yield of butyric acid (g/L) | Yield of acetic acid (g/L) | Ratio of butyric acid and acetic acid (butyric acid/acetic acid) |
|---|---|---|---|---|
| ITRI04005 | 8.23 | 3.79 | 0.83 | 4.6 |
| ITRI05027 | 7.11 | 3.19 | 0.29 | 11 |

(2-3) Genetically Modified Strain "being Able to Express an Exogenous Gene or Having an Endogenous Gene with an Enhanced Expression Level, Wherein Each of the Exogenous Gene and the Endogenous Gene is a Gene of a Heat Shock Protein (HSP)"

(2-3-1) Plasmid Cloning and Verification

Figure 5A:
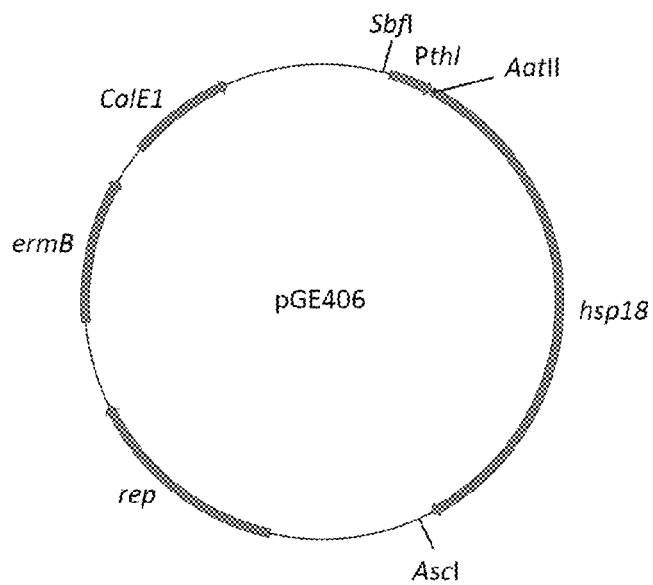
FIGS. 5A and 5B illustrate the pGE406 recombinant plasmid carrying hsp18 and the pGE407 recombinant plasmid carrying groESL, respectively.
Figure 5B:
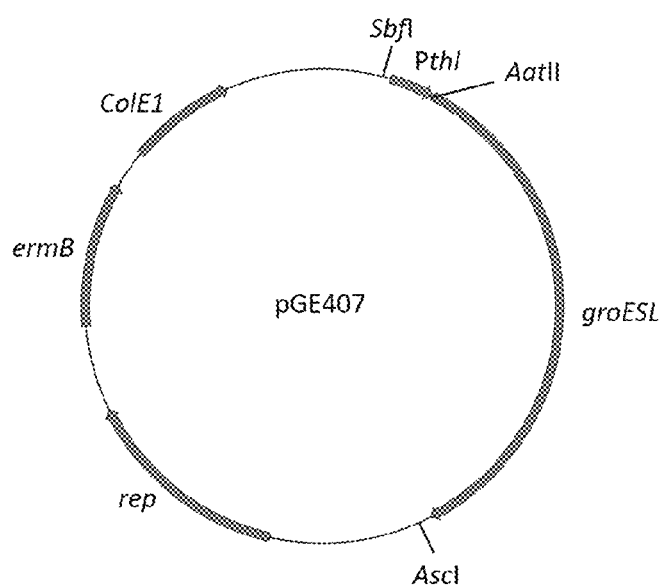

The DNA fragment of groESL gene in genomic DNA of Clostridium cadaveris ITRI04005 was amplified by PCR in combination with the specific primers as shown in Table 10 (i.e., #354 (carrying the AatII restriction site); #355 (carrying the AscI restriction site)), and then an agarose gel electrophoresis was conducted to purify and isolate the amplified "groESL" fragment. In addition, the DNA fragment of hsp18 gene in genomic DNA of *Clostridium cadaveris* ITRI04005 was amplified by PCR in combination with the specific primers as shown in Table 10 (i.e., #356 which carries the AatII restriction site; #357 which carries the AscI restriction site), and then an agarose gel electrophoresis was conducted to purify and isolate the amplified "hsp18" fragment. Thereafter, the amplified "groESL" fragment and "hsp18" fragment were cloned into pCR2.1 vector, and AatII and Asc I restriction enzymes were used to recombine the "groESL" fragment and the "hsp18" fragment to a shuttle vector to obtain recombinant plasmids pGE406 and pGE407, respectively (as shown in FIGS. 5A and 5B). Then, the recombinant plasmids pGE406 and pGE407 were extracted and transformed into *Clostridium cadaveris* ITRI04005 by electroporation genetic transformation technology (each pulse: voltage (2.5 kV); resistance (600Ω); capacity (25 μF)) respectively.

Thereafter, an erythromycin (its final concentration was 50 μg/ml)-containing RCM medium was used to select the genetically modified strain, wherein the strain that could survive in the aforementioned medium might carry the aforementioned recombinant plasmid pGE406 or pGE407.

Then, colony PCR was conducted on the above two genetically modified strains by using the specific primers as shown in Table 10 (i.e., primers for amplifying the groESL fragment: #354, #355; primers for amplifying the hsp18 fragment: #356, #357), and then an agarose gel electrophoresis was conducted to confirm whether the specific PCR product had been produced. By way of the aforementioned PCR in combination with specific primers, it was confirmed that the strains had indeed carried the recombinant plasmid pGE406 or pGE407. That is, the two strains had indeed carried the hsp18 gene or groESL gene (i.e., the twos strains were able to express an exogenous gene or having an endogenous gene with an enhanced expression level, wherein each of the exogenous gene and the endogenous gene was a gene of a heat shock protein (HSP)). The two genetically modified strains were named as *Clostridium cadaveris* ITRI05023 (i.e., a strain being able to express an exogenous gene or having an endogenous gene with an enhanced expression level, wherein each of the exogenous gene and the endogenous gene is hsp18 gene) and *Clostridium cadaveris ITRI*05025 (i.e., a strain being able to express an exogenous gene or having an endogenous gene with an enhanced expression level, wherein each of the exogenous gene and the endogenous gene is groESL gene), respectively.

TABLE 10

| Primer name | Nucleotide sequence of the primer | Sequence number |
|---|---|---|
| #354 | 5'-GGGACGTCATGTTTGATTTA GTACCTTT-3' | SEQ ID NO: 16 |
| #355 | 5'-GGGCGCGCCCTAGTGGATA TCTATAGA-3' | SEQ ID NO: 17 |
| #356 | 5'-GGGACGTCATGAATATTGA CCACTTGG-3' | SEQ ID NO: 18 |
| #357 | 5'-GGGCGCGCCTTAGTACATTC CATCCATA-3' | SEQ ID NO: 19 |

(2-3-2) Test of the Tolerances of Genetically Modified Strains to Fermentation Products (A) Pre-Culture RCM medium was mixed with erythromycin and glucose to provide a medium mixture with an erythromycin concentration of 50 ng/ml and a glucose concentration of 10 g/L. The medium mixture was deoxygenated. Thereafter, each of 50 ml centrifuge tubes were injected with three 20 ml of the deoxygenated medium mixture, and the first one was inoculated with *Clostridium cadaveris* ITRI04005 (hereinafter referred to as "control group" carrying a vector which do not carry the gene desired to be cloned), the second one was inoculated with ITRI05023 (carrying the pGE406 plasmid), and the third one was inoculated with ITRI05025 (carrying the pGE407 plasmid). The three tubes were kept in an aerobic incubator at 37° C. for about 14 to 16 hours such that the strains contained therein entered the mid-log growth phase (i.e., the $OD_{600}$ reached about 1.0 to 1.2).

(B) Preparation of Medium Mixtures

A medium mixture with a glucose concentration of 10 g/L and an erythromycin concentration of 50 μg/ml was prepared by mixing CGM medium, glucose and erythromycin, and then was deoxygenated. Another medium mixture with a glucose concentration of 5 g/L and an erythromycin concentration of 50 μg/ml was prepared by mixing CGM medium, glucose and erythromycin, and then was deoxygenated as well.

(C) Test of Tolerance to Fermentation Products (1)

Each of three 50 ml centrifuge tubes was injected with 25 ml of the deoxygenated medium mixture (the concentration of glucose was 10 g/L), and the first tube was inoculated with the pre-cultured *Clostridium cadaveris* ITRI04005, the second tube was inoculated with ITRI05023, and the first tube was inoculated with ITRI05025. The three tubes were kept in an anaerobic incubator at 37° C. for about 6 hours. Thereafter, sodium butyrate was added into each of the three tubes until the concentration of sodium butyrate in the medium mixture was 10 g/L (hereinafter referred to as "sodium butyrate added" experimental group). Then, the three tubes were kept in an anaerobic incubator at 37° C. to perform fermentation for about 32 hours. The components of organic compounds in the medium mixture after fermentation were analyzed by Agilent 1100 HPLC analysis in combination with Aminex HPX-87H (300×7.8 mm) column. The amount of butyric acid in the medium mixture after fermentation was determined, and the amount of butyric acid produced by fermentation could be obtained by deducting the amount of butyric acid provided by the externally added sodium butyrate from the determined amount of butyric acid.

The above experiments were repeated, with the exception that no sodium butyrate was used (hereinafter referred to as the "free of sodium butyrate" control group).

The yield of butyric acid of the "free of sodium butyrate" control group was set as 100% to calculate the relative yield of butyric acid (%) of the "sodium butyrate added" experimental group. The results are shown in FIG. 6.

Figure 6:
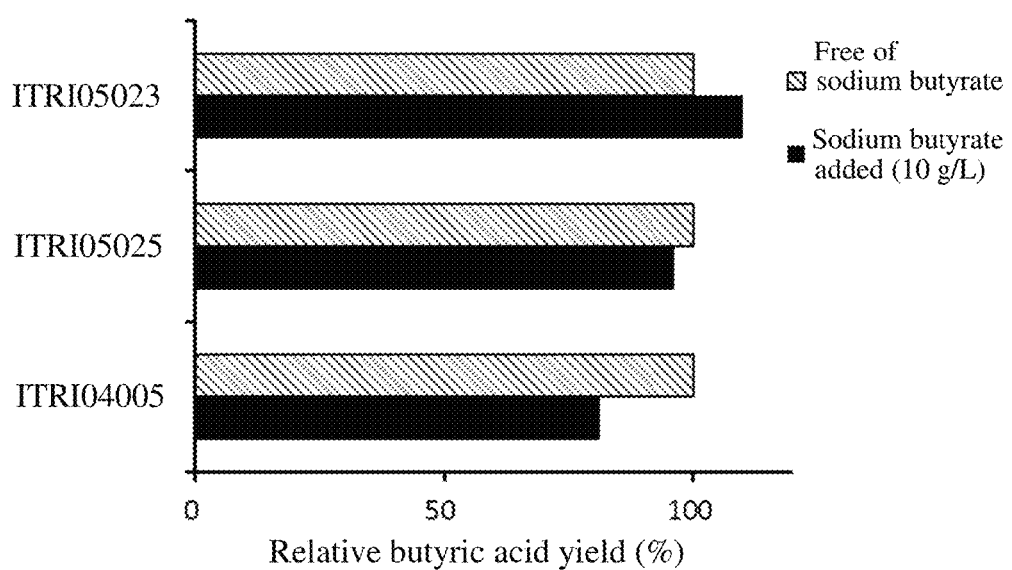
FIG. 6 is a bar diagram showing the relative yields of butyric acid obtained by incubating *Clostridium cadaveris* ITRI04005, ITRI05023, or ITRI05025 in a CGM medium with 10 g/L of sodium butyrate or free of sodium butyrate under an anaerobic atmosphere to perform fermentation.

As shown in FIG. 6, as compared with *Clostridium cadaveris* ITRI04005 of the "free of sodium butyrate" control group, the yield of butyric acid of *Clostridium cadaveris* ITRI04005 of the "sodium butyrate added" experimental group decreased by 20%. However, as compared with *Clostridium cadaveris* ITRI05025 of the "free of sodium butyrate" control group, the yield of butyric acid of *Clostridium cadaveris* ITRI05025 of the "sodium butyrate added" experimental group only decreased by 4%. Furthermore, as compared with *Clostridium cadaveris* ITRI05023 of the "free of sodium butyrate" control group, the yield of butyric acid of *Clostridium cadaveris* ITRI05023 of the "sodium butyrate added" experimental group did not decrease but increased by about 10%. These results indicate that as compared with the strain which had not been genetically modified, genetically modified *Clostridium cadaveris* ITRI05023 and ITRI05025 both had better tolerance to the fermentation products.

(C) Test of Tolerance to Fermentation Products (2)

Figure 7A:
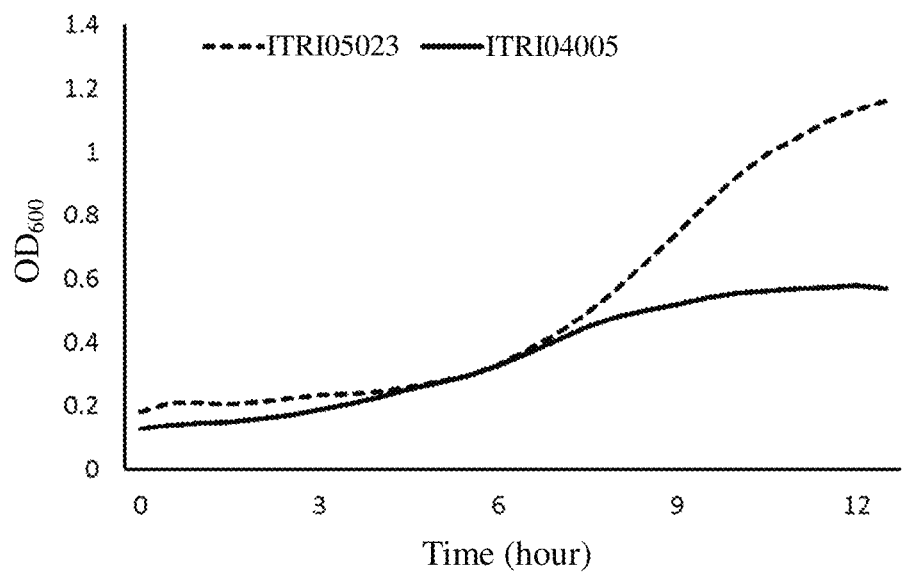

A 24-well plate was injected with the deoxygenated medium mixture (the concentration of glucose was 5 g/L) at a volume of 1.5 ml/well. Sodium butyrate was added into the injected medium mixture at a concentration of 10 g/L, and each well was inoculated with the pre-cultured *Clostridium cadaveris* ITRI04005 or ITRI05023 at a 2% inoculation rate. The plate was kept in a temperature controllable (37° C.) TECAN microplate reader that could provide an anaerobic atmosphere, to perform fermentation. $OD_{600}$ of the medium mixtures were measured every 30 minutes to monitor the growth of the strains. The results are shown in FIG. 7A. The above experiments were repeated, with the exception that the concentration of sodium butyrate in the injected medium mixture was 15 g/L. The results are shown in FIG. 7B.

Figure 7B:
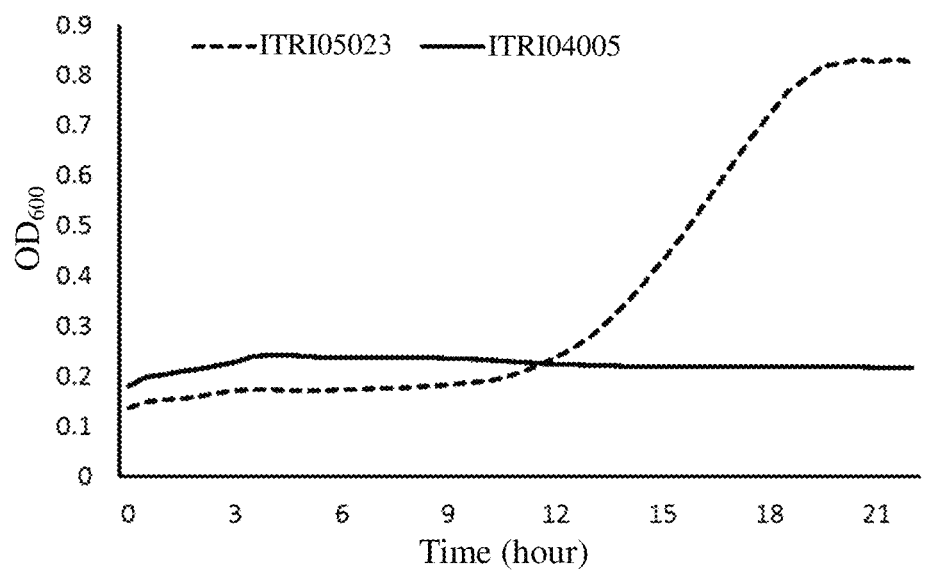

As shown in FIGS. 7A and 7B, no matter whether the concentration of sodium butyrate in the medium mixture was 10 g/L or 15 g/L, as compared with *Clostridium cadaveris* ITRI04005, the growth rate of *Clostridium cadaveris* ITRI05023 was significantly higher. These results indicate again that as compared with a wild type strain which had not been genetically modified, the genetically modified strains of the present invention "being able to express an exogenous gene or having an endogenous gene with an enhanced expression level, wherein each of the exogenous gene and the endogenous gene was a gene of a heat shock protein (HSP)" was more tolerant to the fermentation products.

As shown in the above experimental results, *Clostridium cadaveris* ITRI04005 of the present invention is capable of using saccharide(s) and/or amino acid(s) as the substrate to perform fermentation and produce such as an organic acid or an alcohol as the fermentation product, and thus is a strain capable of using various feedstock sources to produce chemicals or biofuels. Furthermore, through genetic modification, a genetically modified strain meeting the following requirements can be provided from the *Clostridium cadaveris* ITRI04005 of the present invention: (i) being capable of using saccharide(s) and/or amino acid(s) as the substrate to perform fermentation and to produce an organic acid or an alcohol, (ii) having a high specificity of fermentation product, and/or (iii) having a high tolerance to the products. The genetically modified strains are beneficial to providing a good yield of the target product.

BRIEF DESCRIPTION OF REFERENCE NUMERALS

Not applicable.

DEPOSIT OF BIOLOGICAL MATERIAL

Depository institute: DSMZ (Deutsche Sammlung von Mikroorganismen and Zellkulturen GmbH)
Address: Inhoffenstraβe 7 B, 38124 Braunschweig, GERMANY
Date: Jun. 26, 2015
Deposited biological material: *Clostridium cadaveris* ITRI04005
Accession number: DSM 32078

What is claimed is:

1. An isolated *Clostridium cadaveris* ITRI04005, deposited at German Collection of Microorganisms and Cell Cultures (Deutsche Sammlung von Mikroorganismen and Zellkulturen GmbH, DSMZ) under the accession number DSM 32078.

2. A genetically modified strain obtained from the *Clostridium cadaveris* ITRI04005 as claimed in claim 1 by a genetic modification, wherein the genetically modified strain meets at least one of the following requirements:
   (a) expressing an exogenous gene or having an endogenous gene with an enhanced expression level, wherein each of the exogenous gene and the endogenous gene is alcohol dehydrogenase (adh);
   (b) having an endogenous gene with an attenuated expression level or without any expression level, wherein the endogenous gene is at least one of phosphate acetyltransferase (pta) and acetate kinase (ack); and
   (c) expressing an exogenous gene or having an endogenous gene with an enhanced expression level, wherein each of the exogenous gene and the endogenous gene is at least one of heat shock protein 18 (hsp18) and groESL.

3. The genetically modified strain as claimed in claim 2, which meets requirement (a).

4. The genetically modified strain as claimed in claim 2, which meets at least one of requirements (b) and (c).

5. The genetically modified strain as claimed in claim 2, which has a 16S rRNA fragment of SEQ ID NO: 1 or a 16S rRNA fragment having at least 95% identity to the SEQ ID NO: 1.

6. A method of producing an organic acid, comprising:
   providing a substrate; and
   subjecting the genetically modified strain as claimed in claim 4 to use the substrate under an anaerobic atmosphere to perform fermentation.

7. The method as claimed in claim 6, wherein the organic acid is butyric acid.

8. The method as claimed in claim 6, wherein the genetically modified strain has an endogenous gene with an attenuated expression level or without any expression level, and the endogenous gene is a gene of an enzyme participating in a synthesis of acetic acid, and the organic acid comprises butyric acid and acetic acid at a butyric acid/acetic acid weight ratio (B/A ratio) of more than 10.

9. The method as claimed in claim 6, wherein the substrate comprises a saccharide, an amino acid, or a combination thereof.

10. A method of producing an alcohol, comprising:
    providing a substrate; and
    subjecting the genetically modified strain as claimed in claim 3 to use the substrate under an anaerobic atmosphere to perform fermentation.

11. The method as claimed in claim 10, wherein the substrate comprises a saccharide, an amino acid, or a combination thereof.

12. The method as claimed in claim 10, wherein the alcohol is butanol.

13. A method of producing an organic acid, comprising:
    providing a substrate; and
    subjecting the *Clostridium cadaveris* ITRI04005 as claimed in claim 1 to use the substrate under an anaerobic atmosphere to perform fermentation.

14. The method as claimed in claim 13, wherein the organic acid is butyric acid.

15. The method as claimed in claim 13, wherein the substrate comprises a saccharide, an amino acid, or a combination thereof.

* * * * *

SEQUENCE LISTING

```
<160> NUMBER OF SEQ ID NOS: 19

<210> SEQ ID NO 1
<211> LENGTH: 1517
<212> TYPE: DNA
<213> ORGANISM: Clostridium cadaveris
<220> FEATURE:
<223> OTHER INFORMATION: 16S rRNA fragment

<400> SEQUENCE: 1
ttttaaattg agagtttgat cctggctcag gatgaacgct ggcggcgtgc ttaacacatg      60
caagtcgagc gagggagcac cttcgggtgt gaactagcgg cggacgggtg agtaacacgt     120
gggcaacctg ccttacagag ggggatagcc ttccgaaagg aagattaata ccgcatatta     180
tgattttcct gcatgggaaa gtcatgaaag gagcaatccg ctgtaagatg ggcccgcggc     240
gcattagcta gttggtgagg taaggctca ccaaggcgac gatgcgtagc cgacctgaga      300
gggtgatcgg ccacattggg actgagacac ggcccagact cctacgggag gcagcagtgg     360
ggaatattgc acaatggggg aaaccctgat gcagcaacgc cgcgtgagtg atgacggcct     420
tcgggttgta aagctctgtc ttcagggacg ataatgacgg tacctgagga ggaagccacg     480
gctaactacg tgccagcagc cgcggtaata cgtaggtggc gagcgttatc cggatttact     540
gggcgtaaag gatgcgtagg tggaatttta agtgggatgt gaaatacccg ggctcaacct     600
gggaactgca ttccaaactg gaattctaga gtgcaggaga ggaaagcgga attcctagtg     660
tagcggtgaa atgcgtagag attaggaaga acaccagtgg cgaaggcggc tttctggact     720
gtaactgaca ctgaggcatg aaagcgtggg gagcaaacag gattagatac cctggtagtc     780
cacgccgtaa acgatgggta ctaggtgtag gggtttcgat acctctgtgc cgccgtaaac     840
```

-continued

```
acaataagta ccccgcctgg ggagtacggt cgcaagatta aaactcaaag gaattgacgg    900
gggcccgcac aagtagcgga gcatgtggtt taattcgaag caacgcgaag aaccttacct    960
agacttgaca tgtcctgaat tacctgtaat aagggaagct ctttcgggag caggaacaca   1020
ggtggtgcat ggttgtcgtc agctcgtgtc gtgagatgtt gggttaagtc ccgcaacgag   1080
cgcaacccct atagttagtt gctaacagta agatgagcac tctagctaga ctgccgtggt   1140
taacgcggag gaaggtgggg atgacgtcaa atcatcatgc cccttatgtc tagggctaca   1200
cacgtgctac aatggcgaga acaaagagaa gcaagaccgc gaggtggagc aaaactcata   1260
aaactcgtcc cagttcggat tgcaggctgc aactcgcctg catgaagccg gagttactag   1320
taatcgcgaa tcagaatgtc gcggtgaata cgttcccggg ccttgtacac accgcccgtc   1380
acaccatgag agttggcaat acccaaagtc cgtgaggtaa ccgaaaggag ccagcggcct   1440
aaggtagggt cagcgattgg ggtgaagtcg taacaaggta gccgtaggag aacctgcggc   1500
tggatcacct cctttct                                                  1517

<210> SEQ ID NO 2
<211> LENGTH: 17
<212> TYPE: DNA
<213> ORGANISM: artificial sequence
<220> FEATURE:
<223> OTHER INFORMATION: synthetic nucleotide sequence

<400> SEQUENCE: 2
aacgcgaaga accttac                                                    17

<210> SEQ ID NO 3
<211> LENGTH: 15
<212> TYPE: DNA
<213> ORGANISM: artificial sequence
<220> FEATURE:
<223> OTHER INFORMATION: synthetic nucleotide sequence

<400> SEQUENCE: 3 acgggggtg tgtac                                                       15

<210> SEQ ID NO 4
<211> LENGTH: 20
<212> TYPE: DNA
<213> ORGANISM: artificial sequence
<220> FEATURE:
<223> OTHER INFORMATION: synthetic nucleotide sequence

<400> SEQUENCE: 4
gcggcgtgcy taayacatgc                                                 20

<210> SEQ ID NO 5
<211> LENGTH: 20
<212> TYPE: DNA
<213> ORGANISM: artificial sequence
<220> FEATURE:
<223> OTHER INFORMATION: synthetic nucleotide sequence

<400> SEQUENCE: 5
gggttgcgct cgttgcrgga                                                 20

<210> SEQ ID NO 6
<211> LENGTH: 33
<212> TYPE: DNA
<213> ORGANISM: artificial sequence
<220> FEATURE:
```

-continued

<223> OTHER INFORMATION: synthetic nucleotide sequence

<400> SEQUENCE: 6
gcgacgtcat gaaagttaca aatcaaaaag aac                33

<210> SEQ ID NO 7
<211> LENGTH: 32
<212> TYPE: DNA
<213> ORGANISM: artificial sequence
<220> FEATURE:
<223> OTHER INFORMATION: synthetic nucleotide sequence

<400> SEQUENCE: 7
cgggattcat aatgaagcaa agactatttt ac                 32

<210> SEQ ID NO 8
<211> LENGTH: 18
<212> TYPE: DNA
<213> ORGANISM: artificial sequence
<220> FEATURE:
<223> OTHER INFORMATION: synthetic nucleotide sequence

<400> SEQUENCE: 8
ctttaatagt ttgtggtt                                 18

<210> SEQ ID NO 9
<211> LENGTH: 18
<212> TYPE: DNA
<213> ORGANISM: artificial sequence
<220> FEATURE:
<223> OTHER INFORMATION: synthetic nucleotide sequence

<400> SEQUENCE: 9
ttatttcctc ccgttaaa                                 18

<210> SEQ ID NO 10
<211> LENGTH: 18
<212> TYPE: DNA
<213> ORGANISM: artificial sequence
<220> FEATURE:
<223> OTHER INFORMATION: synthetic nucleotide sequence

<400> SEQUENCE: 10
gtaaaacgac ggccagtg                                 18

<210> SEQ ID NO 11
<211> LENGTH: 23
<212> TYPE: DNA
<213> ORGANISM: artificial sequence
<220> FEATURE:
<223> OTHER INFORMATION: synthetic nucleotide sequence

<400> SEQUENCE: 11
gaagcagaaa ttgaaaatct agc                           23

<210> SEQ ID NO 12
<211> LENGTH: 20
<212> TYPE: DNA
<213> ORGANISM: artificial sequence
<220> FEATURE:
<223> OTHER INFORMATION: synthetic nucleotide sequence -continued

<400> SEQUENCE: 12
tatggcagca cctttagagt                                              20

<210> SEQ ID NO 13
<211> LENGTH: 20
<212> TYPE: DNA
<213> ORGANISM: artificial sequence
<220> FEATURE:
<223> OTHER INFORMATION: synthetic nucleotide sequence

<400> SEQUENCE: 13
attatagggg ctaaagctgg                                              20

<210> SEQ ID NO 14
<211> LENGTH: 26
<212> TYPE: DNA
<213> ORGANISM: artificial sequence
<220> FEATURE:
<223> OTHER INFORMATION: synthetic nucleotide sequence

<400> SEQUENCE: 14
cccgggtgat tgttatggat tataag                                       26

<210> SEQ ID NO 15
<211> LENGTH: 25
<212> TYPE: DNA
<213> ORGANISM: artificial sequence
<220> FEATURE:
<223> OTHER INFORMATION: synthetic nucleotide sequence

<400> SEQUENCE: 15
cccgggttaa ctatttatca attcc                                        25

<210> SEQ ID NO 16
<211> LENGTH: 28
<212> TYPE: DNA
<213> ORGANISM: artificial sequence
<220> FEATURE:
<223> OTHER INFORMATION: synthetic nucleotide sequence

<400> SEQUENCE: 16
gggacgtcat gtttgattta gtaccttt                                     28

<210> SEQ ID NO 17
<211> LENGTH: 27
<212> TYPE: DNA
<213> ORGANISM: artificial sequence
<220> FEATURE:
<223> OTHER INFORMATION: synthetic nucleotide sequence

<400> SEQUENCE: 17
gggcgcgccc tagtggatat ctataga                                      27

<210> SEQ ID NO 18
<211> LENGTH: 28
<212> TYPE: DNA
<213> ORGANISM: artificial sequence
<220> FEATURE:
<223> OTHER INFORMATION: synthetic nucleotide sequence

<400> SEQUENCE: 18
gggacgtcat gaatattaga ccacttgg                                     28

<210> SEQ ID NO 19

```
<211> LENGTH: 28
<212> TYPE: DNA
<213> ORGANISM: artificial sequence
<220> FEATURE:
<223> OTHER INFORMATION: synthetic nucleotide sequence

<400> SEQUENCE: 19
gggcgcgcct tagtacattc catccata                                              28
```